(12) United States Patent
Planche et al.

(10) Patent No.: US 12,014,815 B2
(45) Date of Patent: Jun. 18, 2024

(54) SYSTEMS AND METHODS FOR RECORDING MEDICAL ENVIRONMENTS

(71) Applicant: Shanghai United Imaging Intelligence Co., Ltd., Shanghai (CN)

(72) Inventors: Benjamin Planche, Briarwood, NY (US); Ziyan Wu, Lexington, MA (US); Meng Zheng, Cambridge, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 77 days.

(21) Appl. No.: 17/869,852

(22) Filed: Jul. 21, 2022

(65) Prior Publication Data

US 2024/0029867 A1    Jan. 25, 2024

(51) Int. Cl.
*G16H 30/40* (2018.01)
*G06T 19/00* (2011.01)
*H04N 13/189* (2018.01)

(52) U.S. Cl.
CPC ............ *G16H 30/40* (2018.01); *G06T 19/00* (2013.01); *H04N 13/189* (2018.05)

(58) Field of Classification Search
CPC ....... G16H 30/40; G06T 19/00; H04N 13/189
See application file for complete search history.

(56) References Cited

U.S. PATENT DOCUMENTS 7,121,832 B2    10/2006  Hsieh et al.
10,108,266 B2   10/2018  Banerjee et al.
11,195,340 B2   12/2021  Devam et al.
2019/0094981 A1*  3/2019  Bradski ................ H04N 21/414
2022/0030162 A1*  1/2022  Cramer .................. G16H 50/50

FOREIGN PATENT DOCUMENTS

EP         3520385 B1      8/2019

OTHER PUBLICATIONS

M. Loper et al. "SMPL: a skinned multi-person linear model," ACM Trans. Graph., vol. 34, No. 6, p. 248:1-248:16, Oct. 2015.
"Surgeon Simulator: Experience Reality," https://www.meta.com/experiences/pcvr/1014328505355842/.
M. Ros et al. "From stereoscopic recording to virtual reality headsets: Designing a new way to learn surgery," Neurochirurgie, vol. 63, No. 1, pp. 1-5, Mar. 2017.

* cited by examiner

*Primary Examiner* — Chong Wu
(74) *Attorney, Agent, or Firm* — Zhong Law LLC (57) ABSTRACT

Described herein are systems, methods, and instrumentalities associated with generating a multi-dimensional representation of a medical environment based on images of the medical environments. Various pre-processing and/or post-processing operations may be performed to supplement and/or improve the multi-dimensional representation. These operations may include determining semantic information associated with the medical environment based on the images and adding the semantic information to the multi-dimensional representation in addition to space and time information. The operations may also include anonymizing a person presented in the multi-dimensional representation, adding synthetic views to the multi-dimensional representation, improving the quality of the multi-dimensional representation, etc. The multi-dimensional representation of the medical environment generated using these techniques may allow a user to experience and explore the medical environment, for example, via a virtual reality device.

20 Claims, 6 Drawing Sheets

SYSTEMS AND METHODS FOR RECORDING MEDICAL ENVIRONMENTS

BACKGROUND

Practicing a medical procedure such as a surgical procedure requires extensive knowledge and firsthand experience. To gain such knowledge or experience, medical professionals (e.g., including medical students) may train on animals or cadavers, use simulation engines, watch video recordings, and, in recent years, begin to use virtual reality (VR) or augmented reality as a medical education tool. VR/AR may have the potential to create realistic environments in which users may experience actual medical procedures performed by experts in the field. Current VR/AR based medical education tools, however, are mostly based on simulations (e.g., using game engines to create interactive surgical environments) or partial recordings of actual procedures (e.g., egocentric 3D video recordings), and cannot provide dense, immersive, allocentric contents or models to replicate the actual procedures. Accordingly, systems, methods, and instrumentalities capable of generating realistic, AR/VR enabling representations of medical procedures or medical environments may be desired.

SUMMARY

Described herein are systems, methods, and instrumentalities associated with generating a multi-dimensional representation of a medical environment (e.g., a stereoscopic rendition of the medical environment) based on images of the medical environments captured by one or more sensing devices (e.g., such as digital cameras). An apparatus configured to perform such a task may include one or more processors configured to obtain a first set of images of the medical environment and a second set of images of the medical environment, wherein the first set of images may be associated with a first viewpoint and the second set of images may be associated with a second viewpoint. The one or more processors may be further configured to determine first semantic information associated with the medical environment based on the first set of images or the second set of images, and to generate a multi-dimensional representation of the medical environment based on at least the first set of images, the second set of images, and the first semantic information. Such a multi-dimensional representation may include multiple views of the medical environment over a time period, wherein a first subset of the multiple views may be associated with the first viewpoint, a second subset of the multiple views may be associated with the second viewpoint, and at least one of the multiple views of the medical environment may include a presentation of the first semantic information. Once generated, the multi-dimensional representation of the medical environment may be provided to a receiving device, for example, such that a user may experience and/or explore the medical environment using a virtual reality (VR) headset.

In examples, the one or more processors of the apparatus described herein may be configured to determine the first semantic information using a machine-learning (ML) model trained for determining a location or a motion of an object or a person in the medical environment based on the first set of images or the second set of images, and the first semantic information may indicate the location or motion of the object or person in the medical environment. In examples, the one or more processors may be further configured to determine a phase of a medical procedure being performed in the medical environment based on the location or motion of the object or person in the medical environment, and wherein the first semantic information may further indicate the phase of the medical procedure. In examples, prior to generating the multi-dimensional representation of the medical environment based on at least the first set of images, the second set of images, and the first semantic information, the one or more processors of the apparatus described herein may be further configured to edit one or more identifying features of a person detected in the first set of images or the second set of images such as the identity and/or likeness of the person may be hidden in the multi-dimensional representation of the medical environment.

In examples, prior to providing the multi-dimensional representation of the medical environment to the receiving device, the one or more processors of the apparatus described herein may be further configured to generate a synthetic view of the medical environment based on a machine-learning model and add the synthetic view of the medical environment to the multi-dimensional representation. Such a synthetic view may depict a scene in the medical environment not shown in the first set of images or the second set of images, and the synthetic view may be associated with a time spot outside the respective time periods associated with the first and second sets of images.

In examples, prior to providing the multi-dimensional representation of the medical environment to the receiving device, the one or more processors of the apparatus described herein may be further configured to increase a resolution of at least one of the multiple views of the medical environment based on a machine-learning model (e.g., a machine-learning model trained for super-resolution). The one or more processors may also be configured to fill a region of at least one of the multiple views of the medical environment based on a machine-learning model, or to determine second semantic information associated with the medical environment and add the second semantic information to the multi-dimensional representation. In examples, the second semantic information may include a medical record of a patient, and the one or more processors may be configured to determine, based on a machine-learning model, an identity of the patient based on the first set of images or the second set of images, and to retrieve the medical record based on the identity of the patient.

BRIEF DESCRIPTION OF THE DRAWINGS

A more detailed understanding of the examples disclosed herein may be had from the following description, given by way of example in conjunction with the accompanying drawing.

DETAILED DESCRIPTION

The present disclosure is illustrated by way of example, and not by way of limitation, in the figures of the accompanying drawings.

Figure 1:
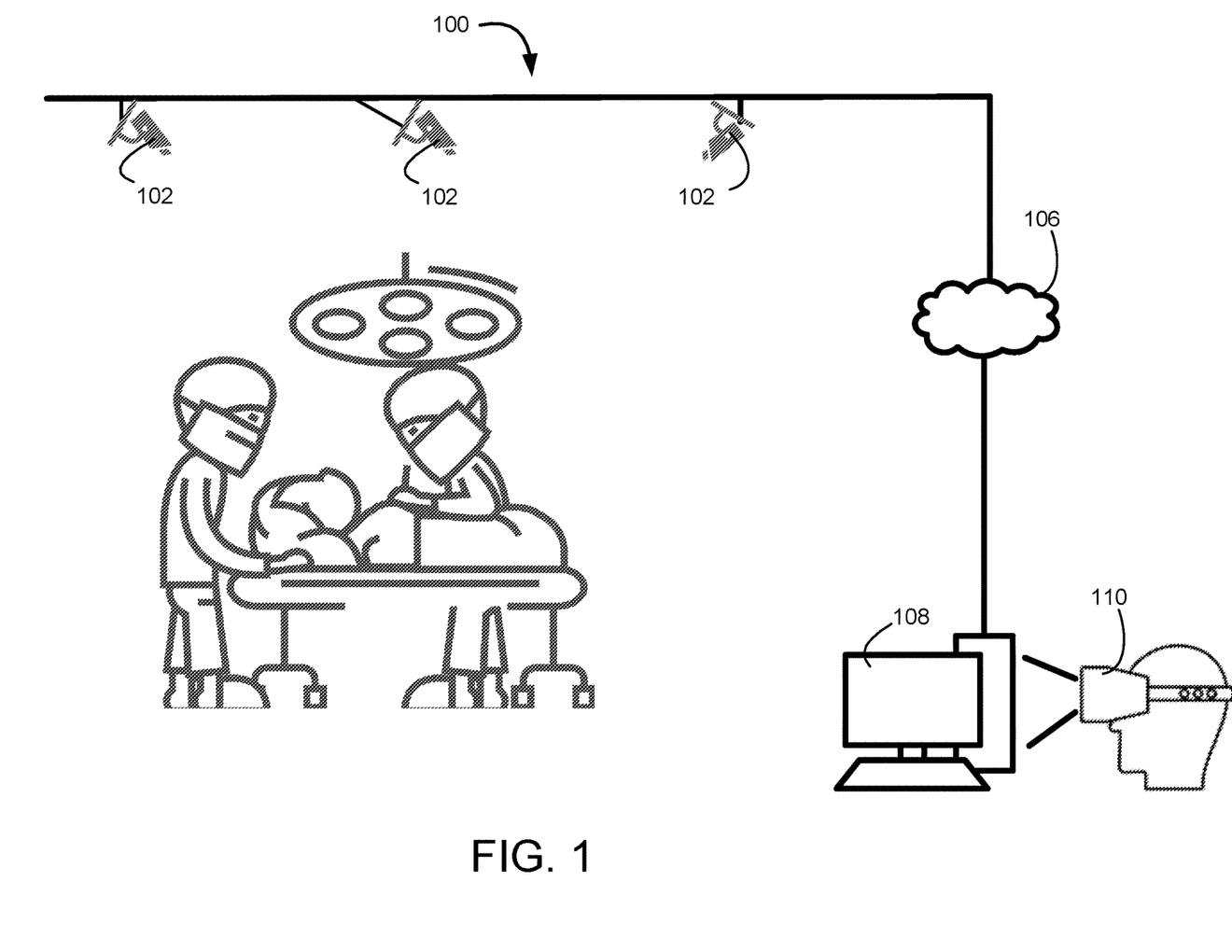
FIG. 1 is a simplified diagram illustrating an example use case of one or more embodiments of the present disclosure.

FIG. 1 illustrates an example use case of the techniques disclosed herein. The use case may involve a medical environment (e.g., 100 in the figure), which may be part of a medical facility such as a scan room (e.g., for magnetic resonance imaging (MRI), X-ray, Computed Tomography (CT), etc.) or an operating room (OR). Medical environment 100 may be equipped with one or more sensing devices 102a-102c that may be installed in different locations of the medical environment and configured to capture images or videos of a medical procedure (e.g., a surgical procedure) being performed in medical environment 100. The images (e.g., two-dimensional (2D) images) or videos may provide different views of the medical environment (e.g., including the medical procedure being performed therein) over a time period and/or from different viewpoints. In examples, sensing devices 102a-c may include one or more sensors such as one or more 2D visual sensors (e.g., 2D cameras), one or more three-dimensional (3D) visual sensors (e.g., 3D cameras), one or more red, green, and blue (RGB) sensors, one or more depth sensors, one or more RGB plus depth (RGB-D) sensors, one or more thermal sensors (e.g., infrared (FIR) or near-infrared (NIR) sensors), one or more radar sensors, and/or other types of image capturing devices or circuitries. In examples, sensing devices 102a-102c may be communicatively coupled (e.g., via communication network 106) to a processing device 108 (e.g., a computer) and/or other devices in medical environment 100, and may be configured to transmit images captured by the sensing devices to the processing device and/or the other devices. In examples, one or more of sensing devices 102a-102c may themselves include a processing or functional unit (e.g., a processor) configured to process the images captured by the sensing devices.

Processing device 108 (or the processing or functional unit of each sensing device 102a-102c) may be configured to obtain (e.g., retrieve or otherwise receive) image data from sensing devices 102a-102c (e.g., as respective first image source, second image source, and third image source), process the image data, and generate a multi-dimensional representation of the medical environment (or the medical procedure performed therein) based on the image data. As will be described in greater detail below, the processing may include pre-processing the image data, modeling the medical environment (or the medical procedure performed therein) based on the pre-processed image data to derive a multi-dimensional representation (MDR) of the medical environment, and post-processing the MDR before providing the MDR to a receiving device. In examples, such a multi-dimensional representation may be used to create a stereo-scopic 3D rendition (e.g., with or without sound) of the medical environment (or the medical procedure performed therein) that a user may experience via virtual reality (VR) device such as VR headset 110 shown in FIG. 1.

In examples, the multi-dimensional representation of the medical environment described herein may include a time dimension (e.g., over the time period associated with the source image data) and one or more spatial dimensions (e.g., the 3D space of medical environment 100) that may provide multiple views of the medical environment spanning a time period and/or from different viewpoints (e.g., a first subset of the multiple views may be associated with a first viewpoint of a first sensing device, a second subset of the multiple views may be associated with a second viewpoint of a second sensing device, etc.). In examples, at least one of the multiple views of the medical environment may include a presentation of semantic information that may be obtained during the pre-processing and/or post-processing operations described herein. Such semantic information may include, for example, information that may identify and/or track a specific object (e.g., an organ, a surgical tool, a medical device, etc.) during the medical procedure, or annotations that may facilitate understanding of the medical procedure (e.g., medical records such as scan images or vitals related to the medical procedure). In examples, the multi-dimensional representation may also include refined or synthesized views of the medical environment (or the medical procedure performed therein) that may be generated using spatial and/or temporal interpolation or extrapolation techniques, de-noising techniques, super-resolution techniques, etc. Based on the multitude of information provided by the multi-dimensional representation, a user may visualize and explore the medical environment or the medical procedure (e.g., the user may be able to virtually move around the environment and/or observe the medical procedure from different viewpoints based on motion tracking and/or manual inputs). The user may also be able to display (e.g., via an interactive VR interface) the semantic information described above, for example, in the form of textual inputs or visual contents overlaid on top of the VR video.

Figure 2:
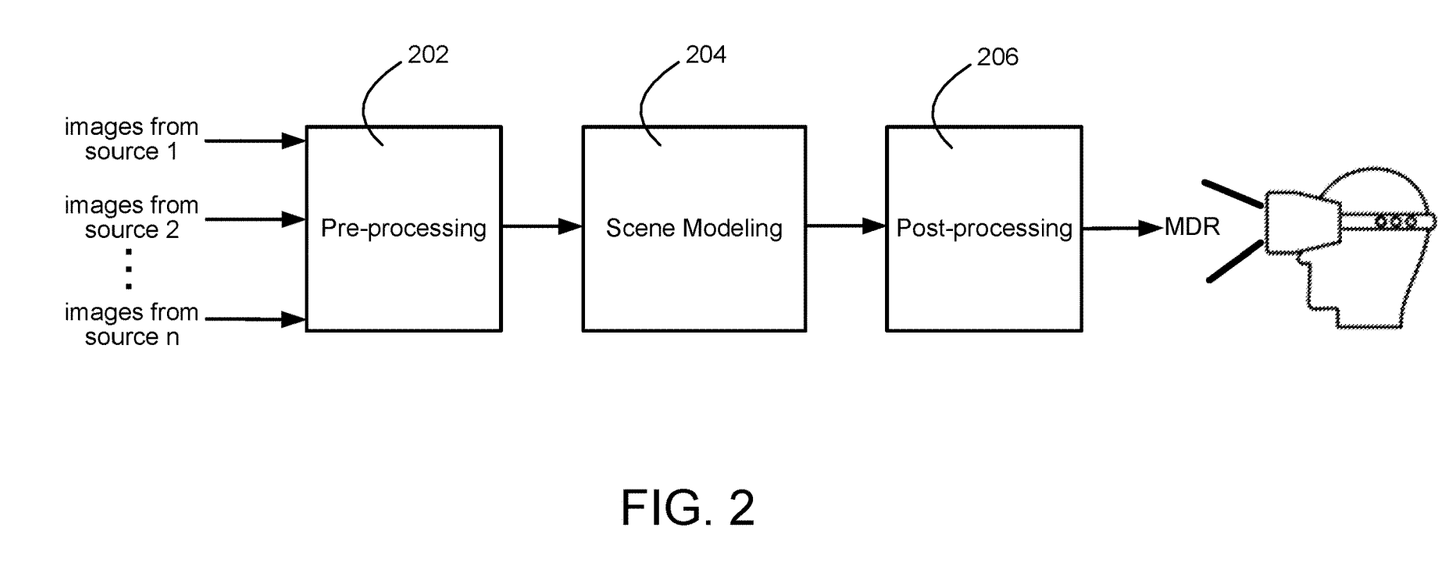
FIG. 2 is a simplified diagram illustrating example operations that may be associated with generating a multi-dimensional representation (MDR) of a medical environment in accordance with one or more embodiments of the present disclosure.

FIG. 2 illustrates example operations that may be associated with generating a multi-dimensional representation (MDR) of a medical environment (including a medical procedure performed therein) in accordance with one or more embodiments of the present disclosure. As shown, the MDR may be generated based on image data obtained from multiple sources (e.g., the sensing devices described herein) that may provide different views of the medical environment (e.g., based on different installation locations of the sensing devices) over a time period. The image data obtained from the multiple sources may be pre-processed at 202 before the pre-processed data is passed for scene modeling at 204. The pre-processing may be performed using various machine-learning (ML) techniques and/or to accomplish various objectives. For instance, the pre-processing may include extracting, using a first ML model, first semantic information associated with the medical environment from one or more of the source image data. Such semantic information may be obtained, for example, by identifying specific objects in the medical environment such as surgical tools, medical devices, the hands of a surgeon, etc., and to track the respective locations and/or motions (e.g., movements) of those objects such that the whereabout of and/or the techniques applied by medical professionals during the medical procedure may be indicated by the first semantic information. In addition, based on the locations and/or motions of the objects, phases of the medical procedure may also be automatically determined based on the image data, from which the MDR may be segmented into sections that may correspond to the determined phases (e.g., one section per operating phase), e.g., to allow selective viewing of a specific phase of the medical procedure.

In examples, the pre-processing may include anonymizing, using a second ML model, people appearing in the image data (e.g., patient(s) and/or medical professionals) such that the identity of the people may be protected in the MDR for privacy purposes. For example, the second ML model may include an image-editing model trained to edit and/or replace certain identifying features (e.g., facial features) of the people appearing in the collected images such that the identity and likeness of the people may be hidden in the MDR without affecting the photo-realistic quality of the representation (e.g., the identifying features of a person may be replaced with artificially generated features).

The scene modeling at 204 may also be accomplished using one or more machine-learning (ML) models. For example, an MDR of the people and/or objects in the medical environment may be constructed using ML model(s) (e.g., artificial neural networks) pre-trained for human, object, and/or scene modeling. Such an MDR may include parameters that may indicate the respective shapes, poses (e.g., if the modeling target is a person), and/or positions of one or more persons or objects in the medical environment. These parameters may be predicted using the pre-trained ML model(s) or neural network(s) based on the images collected from the various image sources, and once predicted, the parameters may be used to construct a visual representation of the medical environment from different viewpoints and/or over a time period. For instance, the MDR may be generated using one or more artificial neural networks (ANNs) that may include a motion estimation neural network, a motion field prediction neural network, and/or a space/time field prediction neural network. The motion estimation neural network may be trained to determine, based on input images captured by the sensing devices described herein, a plurality of features of the medical environment that may indicate respective motions of multiple 3D points in the medical environment from a source time to a target time. The motion field prediction neural network may be trained to determine, based on the plurality of features determined by the motion estimation neural network, a motion field that may indicate respective updated locations of the multiple 3D points in the medical environment at the target time, while the space/time field prediction neural network (e.g., a neural radiance field (NeRF) neural network) may be trained to predict the image properties of the multiple points at the target time and/or in a given viewing direction based on the respective locations of the multiple 3D points indicated by the motion field. Each of these neural networks may include a convolutional neural network or a multi-layer perceptron (MLP) neural network comprising multiple fully-connected layers. Examples of the motion estimation neural network, motion field prediction neural network, and space/time field prediction neural network can be found in commonly assigned U.S. patent application Ser. No. 17/851,494, filed Jun. 28, 2022, entitled "Systems and Methods for Motion Estimation and View Prediction," the disclosure of which is hereby incorporated by reference in its entirety.

The neural network(s) or ML model(s) used to generate the MDR of the medical environment may have the ability to continuously model the radiance (e.g., color) and/or density (e.g., image properties relating to the geometry of a person or object) of a scene in the medical environment, e.g., based on discrete observations (e.g., a set of multi-view images) of the scene. In examples, the neural network(s) or ML model(s) may be further trained to model semantic information of the scene (e.g., such as that determined during the pre-processing stage described herein), together with the radiance and density properties of the scene. Such semantic information may include, for example, the classes or categories of the different entities (e.g., objects and/or persons) in the scene, their bounding boxes, the body pose parameters of the individuals detected in the scene, etc. The neural network(s) or model(s) may acquire (e.g., learn) the ability to perform the modeling task through a training process that may involve using the neural network(s) or ML model(s) to predict 2D views of the scene (e.g., each view may include a 2D image of the scene and corresponding semantic information), comparing the predicted views to real images and corresponding semantic labels (e.g., ground truth), and adjusting parameters of the neural network(s) or ML model(s) to minimize the difference (e.g., loss) between the prediction and the reality. Once trained, the neural network(s) or model(s) may be used to generate intermediary views of the scene such that a continuous representation the scene (e.g., 3D dimensional in space and across time) may be obtained.

In examples, multiple neural fields (e.g., multiple NeRF networks) may be used to model the scene, with a subset of the neural fields optimized to model respective scene entities (e.g., respective persons or objects detected and/or segmented from 2D images during pre-processing), and an additional neural field (e.g., a background neural field) optimized to model the leftover scene entities. Another neural network may then be used to combine results generated by the multiple neural fields into a single view of the scene.

In examples, the MDR of the medical environment may be generated based on discrete 2D images, e.g., by predicting the 3D mesh of the different scene entities (e.g., persons and/or objects) utilizing 3D model regression techniques and/or prior knowledge about the physical characteristics (e.g., average or template shapes) of the target entities (e.g., so that the regression techniques may only have to predict entity-specific deformation of the average or template shapes).

As part of the scene modeling process at 204, images collected from different sources (e.g., from different sensors) may be registered such that the MDR of the medical environment constructed at 204 may be used to provide different views (e.g., across space and time) of the medical environment as reflected by the images collected from the different sources. The image registration operation may include, for example, geometrically aligning two images with different viewing geometry and/or different terrain distortions into a same coordinate system so that corresponding pixels may represent the same objects. In examples, the registration may be accomplished using a feature-based approach, e.g., by locating and matching a number of feature points in a first image (e.g., a base image) and a second image (e.g., a warped image) selected for registration, and computing the parameters of a geometric transformation between the two images based on corresponding feature points. In examples, the registration may be accomplished using an area or pixel-based approach, e.g., by estimating translation, rotation, and scale parameters that may relate the images selected for registration.

The MDR of the medical environment generated at 204 may incorporate the semantic information extracted from and/or the image anonymization accomplished at 202 (e.g., during pre-processing). For example, the MDR of the medical environment may include a dimension (e.g., in addition to space and/or time dimensions) for the extracted semantic information such that a visual representation of the medical environment rendered based on the MDR may include a representation of the semantic information (e.g., certain objects identified and/or tracked in the semantic information may be highlighted in the visual representation). As another example, if the facial features of a person in the source images have been anonymized during pre-processing, the person may also be anonymized in the MDR of the medical environment and in the visual representation of the medical environment rendered based on the MDR.

The MDR of the medical environment generated at 204 may be subject to additional processing (e.g., post-processing) at 206 to improve the quality of the representation. For example, the post-processing may add synthetic views of the medical environment to the MDR based on existing views of the medical environment obtained from the source images. The post-processing may also improve the quality of the existing views (e.g., from certain viewpoints or at certain times), for example, by smoothing those views through super-resolution, filling missing 3D regions in the views (e.g., which may be caused by blocking or occlusion), improving the quality of a 3D representation of a person using a human model regressor (e.g., such as a skinned multi-person linear model (SMPL) based regressor), etc. For example, a synthetic view of the medical environment may be generated using one or more artificial neural networks (e.g., neural fields trained to continuously modelling the radiance, density, and/or semantic properties of the target scene) that may have acquired knowledge about the motion and/or image properties of the medical environment through a training process. Similarly, the quality of the MDR may also be improved using one or more artificial neural networks trained for super-resolution (e.g., to increase the resolution of a visual representation of the MDR) and/or for 3D human model densification (e.g., using a 3D human model regressor). For instance, to compensate for partial occlusion of individuals in the scene, a 3D human mesh regression model may be used to predict (e.g., synthetically fill in) missing parts of a person's body (e.g., body keypoints such as joint locations of the person) in order to obtain a full 3D mesh of the person. The human mesh regression model may recover these missing parts of the person's body based on, for example, the hierarchical structure of the person's body (e.g., kinematic chains), different views of the person's body captured by multiple sensing devices, etc.

The post-processing operation at 206 may also add additional semantic information to the MDR including, for example, a medical history (e.g., previous diagnoses and/or scan images) of a patient depicted in the MDR. For instance, such a medical history may be automatically retrieved from a medical record repository upon determining (e.g., using an ML model) the identity of the patient from the source images or upon recognizing a medical procedure being provided to the patient based on the source images.

The MDR generated through the pre-processing, scene modeling, and/or post-processing process(es) described herein may be provided to a receiving device to generate a visual representation of the medical environment for a user to experience and explore. The visual representation may include multiple views of the medical environment at a given time (e.g., based on respective viewpoints of the sensing devices described herein), and/or views of the medical environment at different points in time (e.g., based on the time span of the input images). The video representation may be stereoscopic (e.g., with or without sound) so as to create a virtual reality that a user may experience using a VR device (e.g., a VR headset). For example, once the MDR of the medical environment is determined, it may be queried to obtain parameters for generating images (e.g., and/or semantic labels) of the medical environment from different viewpoints. These viewpoints may correspond to, for example, the eye positions of an observer such that, given a position of the observer in the environment, stereo-images of the environment may be generated based on the MDR, where the intrinsic and/or extrinsic parameters of the two cameras correspond to the two observing eyes.

Figure 3A:
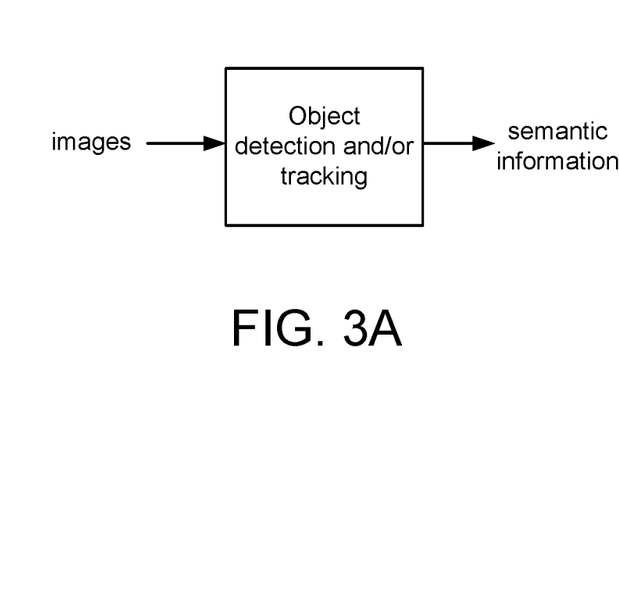
FIG. 3A and FIG. 3B are simplified diagrams illustrating examples of machine-learning (ML) models that may be used to pre-process images of a medical environment in accordance with one or more embodiments of the present disclosure.
Figure 3B:
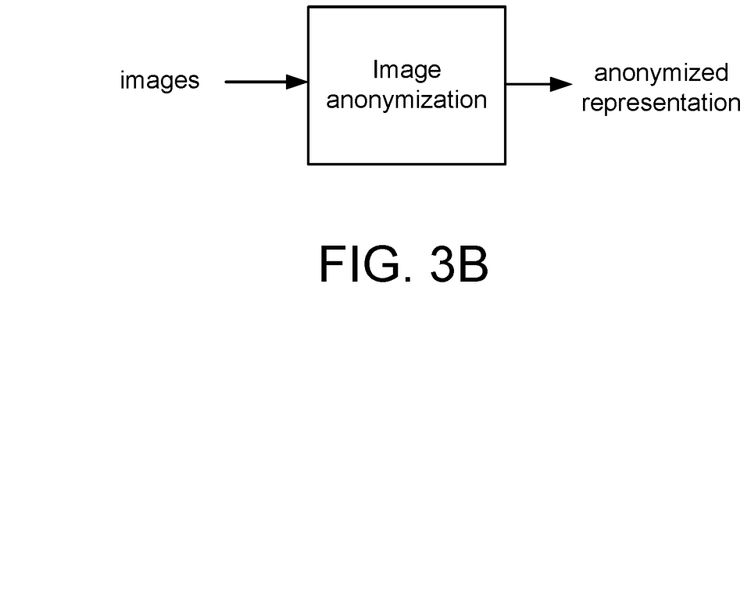

FIG. 3A and FIG. 3B illustrate examples of ML models that may be used during the pre-processing process described herein (e.g., at 202 of FIG. 2). As shown in FIG. 3A, the pre-processing process may utilize a pre-processing ML model trained to identify and/or track an object (e.g., including a person) in the images captured by the sensing devices described herein. Such a pre-processing ML model may be learned and/or implemented using an artificial neural network (ANN) such as a convolutional neural network (e.g., each of the ML models described herein may refer to the structure and/or parameters of the neural network used to learn and/or implement the ML model). In examples, the ANN described herein may include a plurality of layers such as one or more convolution layers, one or more pooling layers, and/or one or more fully connected layers. Each of the convolution layers may include a plurality of convolution kernels or filters configured to extract features from an input image. The convolution operations may be followed by batch normalization and/or line or non-linear activation, and the features extracted by the convolution layers may be down-sampled through the pooling layers and/or the fully connected layers to reduce the redundancy and/or dimension of the features so as to obtain a representation of the down-sampled features (e.g., in the form of a feature vector or feature map). In examples, the ANN described herein may further include one or more un-pooling layers and one or more transposed convolution layers that may be configured to up-sample and de-convolve the features extracted through the operations described above. As a result of the up-sampling and de-convolution, a dense feature representation (e.g., a dense feature map) of the input image may be derived, and the ANN may be trained (e.g., parameters of the ANN may be adjusted) to predict the presence or non-presence of a target object or person in the input image based on the feature representation.

As shown in FIG. 3B, the pre-processing operations described herein may include a pre-processing ML model trained to anonymize one or more persons (e.g., a patient and/or a medical professional) present in an input image. Similar to the first pre-processing ML model, the second pre-processing ML model may also be learned and/or implemented using an artificial neural network. In examples, such an artificial neural network may include a generative adversarial network (GAN) trained to detect human faces in an input image, extract features of the faces (e.g., facial expression, skin color, face illumination, etc.), generate synthetic images of different faces with the same or similar features, and overlay the synthetic face images on top of the corresponding detected faces in the input, e.g., to hide the identities of the persons in the input image.

Figure 4A:
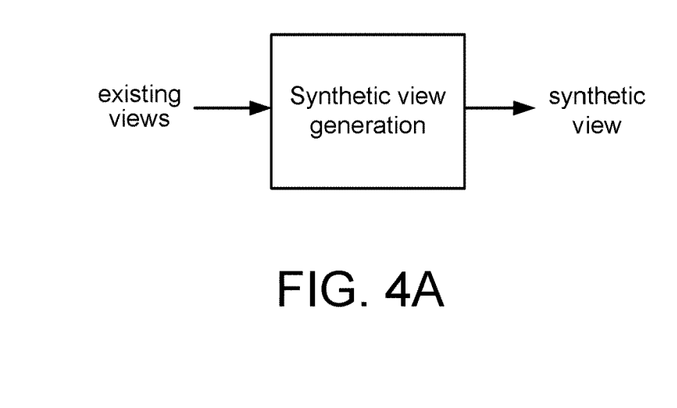
FIG. 4A and FIG. 4B are simplified diagrams illustrating examples of ML models that may be used to post-process a multi-dimensional representation of a medical environment in accordance with one or more embodiments of the present disclosure.
Figure 4B:
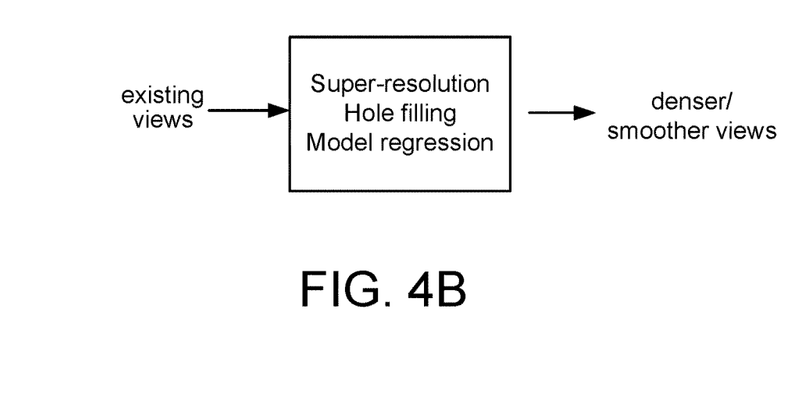

FIG. 4A and FIG. 4B illustrate examples of ML models that may be used during the post-processing process described herein (e.g., at 206 of FIG. 2). As shown in FIG. 4A, the post-processing process may utilize a post-processing ML model trained to generate a synthetic view of a medical environment based on existing views of the medical environment obtained from one or more source images. In examples, such a post-processing ML model may be learned and/or implemented using one or more artificial neural networks (ANNs) including, e.g., a motion estimation neural network, a motion field prediction neural network, and/or a space/time field prediction neural network. The motion estimation neural network may be trained to determine, based on input images captured by the sensing devices described herein, a plurality of features of the medical environment that may indicate respective motions of multiple 3D points in the medical environment from a source time to a target time. The motion field prediction neural network may be trained to determine, based on the plurality of features determined by the motion estimation neural network, a motion field that may indicate respective updated locations of the multiple 3D points in the medical environment at the target time, while the space/time field prediction neural network may be trained to predict the image properties of the multiple points at the target time and/or in a given viewing direction based on the respective locations of the multiple 3D points indicated by the motion field. Each of these neural networks may include a convolutional neural network or a multi-layer perceptron (MLP) neural network comprising multiple fully-connected layers. Examples of the motion estimation neural network, motion field prediction neural network, and space/time field prediction neural network can be found in commonly assigned U.S. patent application Ser. No. 17/851,494, filed Jun. 28, 2022, entitled "Systems and Methods for Motion Estimation and View Prediction," the disclosure of which is hereby incorporated by reference in its entirety As shown in FIG. 4B, the post-processing process may utilize an ML model trained to improve the quality of the multi-dimensional representation (MDR) of the medical environment, for example, through super-resolution. When referred to herein, super-resolution may encompass operations associated with upscaling and enhancing the quality (e.g., resolution) of a visual representation, and an ML model trained for such a purpose may be implemented using an artificial neural network such as a generative adversarial network (GAN) comprising a generator network and a discriminator network (e.g., each of which may include a convolutional neural network as described herein). The generator network may be trained to take as input a low-resolution visual representation and try to predict a high-resolution version of the visual representation. On the other hand, the discriminator network may be trained to predict whether an input representation is a real high-resolution representation or a representation upscaled by the generator. Both networks may be trained together (e.g., simultaneously) with an objective to improve the quality of the prediction made by each network, and once the training is done, the generator network may be used to enhance the quality of the multi-dimensional representation described herein.

Also as shown in FIG. 4B, the post-processing process may utilize an ML model trained for filling missing 3D regions in the MDR. These missing 3D regions may be caused by various reasons including, for example, blocking/occlusion of certain objects in the source images (e.g., parts of a patient's body may be covered by a sheet), poor image quality, object ambiguities, etc. An ML model trained for filling these missing regions may be implemented using an artificial neural network such as the convolutional neural network described herein. For instance, the artificial neural network may be trained to infer contents for a missing region in a certain view of the medical environment (e.g., derived from a first source image) based on knowledge about the mission region learned from another view of the medical environment (e.g., derived from a second source image). As another example, the artificial neural network may be trained to infer contents for a missing region such as a region corresponding the left hand of a person based on the pose and/or body anatomy of the person (e.g., based on the respective positions of the person's left elbow and/or left shoulder). As yet another example, the artificial neural network may be trained to infer contents for a missing region by extracting motion information from the source images and predict the movement and/or location of an object in the missing region. Also as shown in FIG. 4B, the post-processing process may utilize an ML model trained for improve the quality of a human model included in the MDR, for example, using a 3D human model regressor as described herein.

Figure 5:
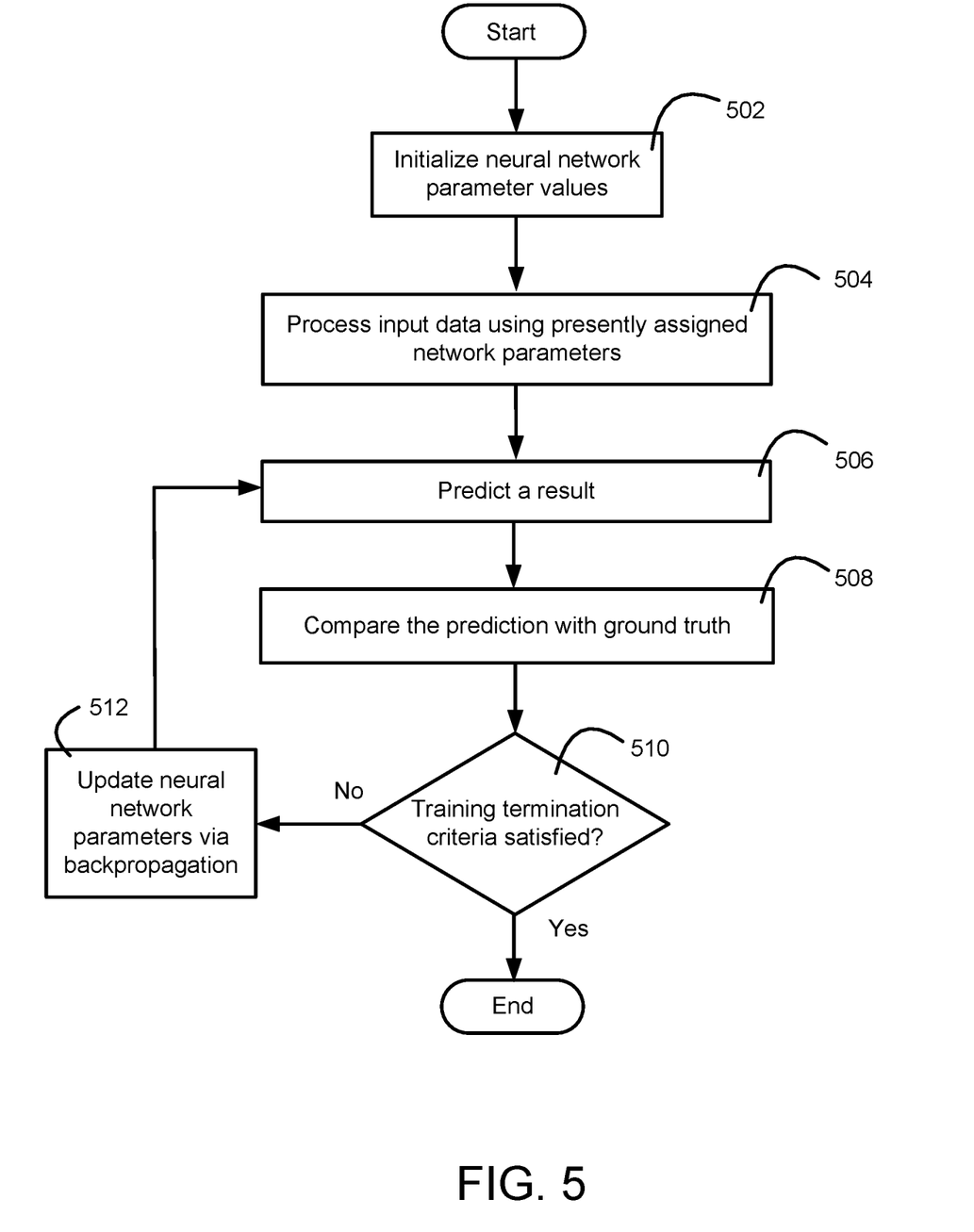
FIG. 5 is a flow diagram illustrating example operations that may be associated with training a neural network (e.g., an ML model implemented by the neural network) for performing a task described in one or more embodiments of the present disclosure.

FIG. 5 illustrates example operations that may be associated with training a neural network (e.g., an ML model implemented by the neural network) for performing one or more of the tasks described herein. As shown, the training operations may include initializing the operating parameters of the neural network (e.g., weights associated with various layers of the neural network) at 502, for example, by sampling from a probability distribution or by copying the parameters of another neural network having a similar structure. The training operations may further include processing an input (e.g., a training image) using presently assigned parameters of the neural network at 504, and making a prediction for a desired result (e.g., a feature vector, a motion field, a classification, etc.) at 506. The prediction result may then be compared to a ground truth at 508 to determine a loss associated with the prediction based on a loss function such as mean squared errors between the prediction result and the ground truth, an L1 norm, an L2 norm, etc. The loss thus calculated may be used to determine, at 510, whether one or more training termination criteria are satisfied. For example, the training termination criteria may be determined to be satisfied if the loss is below a threshold value or if the change in the loss between two training iterations falls below a threshold value. If the determination at 510 is that the termination criteria are satisfied, the training may end; otherwise, the presently assigned network parameters may be adjusted at 512, for example, by backpropagating a gradient descent of the loss function through the network before the training returns to 506.

For simplicity of explanation, the training steps are depicted and described herein with a specific order. It should be appreciated, however, that the training operations may occur in various orders, concurrently, and/or with other operations not presented or described herein. Furthermore, it should be noted that not all operations that may be included in the training process are depicted and described herein, and not all illustrated operations are required to be performed.

Figure 6:
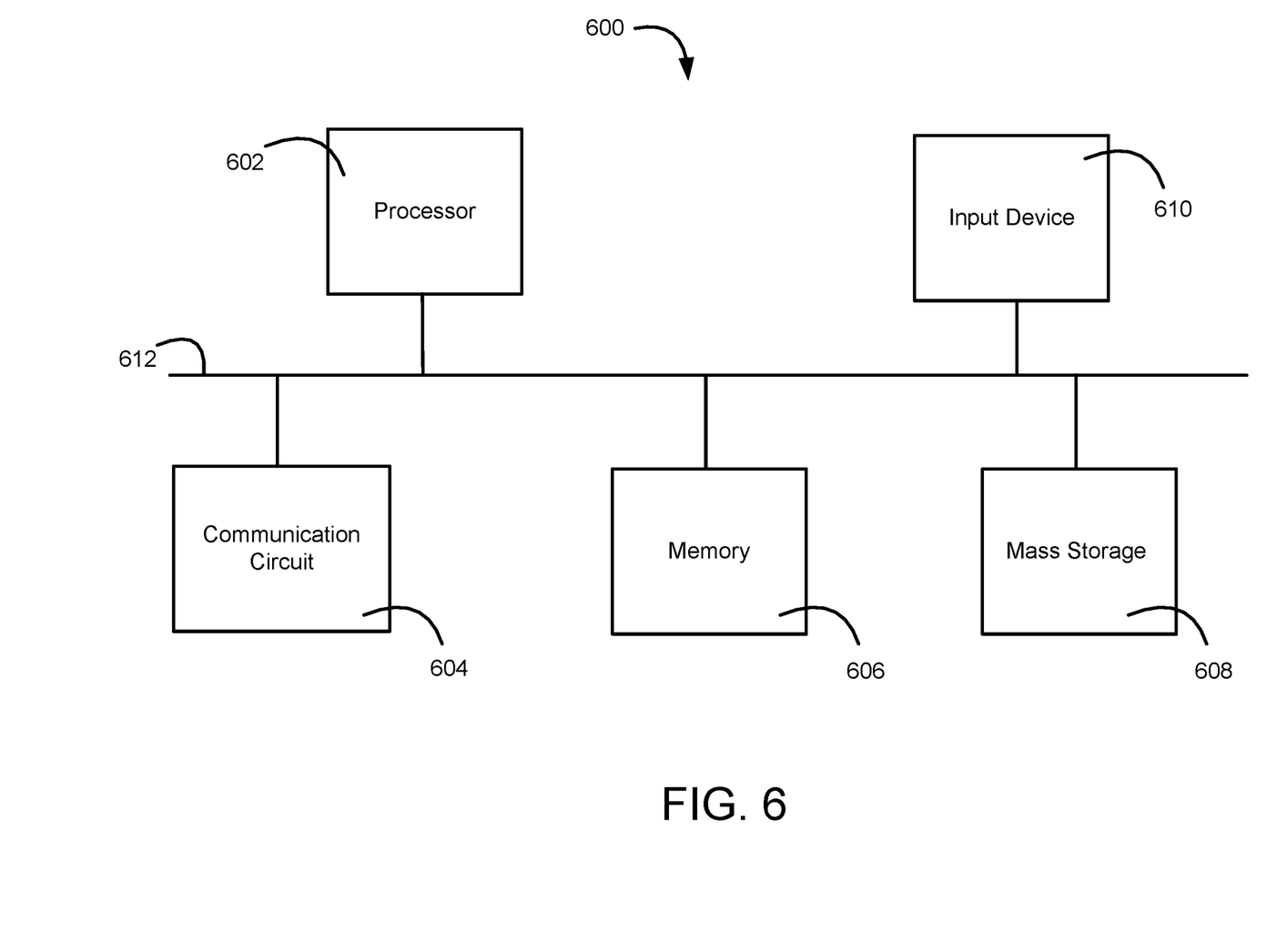
FIG. 6 is a block diagram illustrating example components of an apparatus that may be configured to perform the tasks described in one or more embodiments of the present disclosure.

The systems, methods, and/or instrumentalities described herein may be implemented using one or more processors, one or more storage devices, and/or other suitable accessory devices such as display devices, communication devices, input/output devices, etc. FIG. 6 illustrates an example apparatus 600 that may be configured to perform the tasks described herein. As shown, apparatus 600 may include a processor (e.g., one or more processors) 602, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. Apparatus 600 may further include a communication circuit 604, a memory 606, a mass storage device 608, an input device 610, and/or a communication link 612 (e.g., a communication bus) over which the one or more components shown in the figure may exchange information.

Communication circuit 604 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). Memory 606 may include a storage medium (e.g., a non-transitory storage medium) configured to store machine-readable instructions that, when executed, cause processor 602 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. Mass storage device 608 may include one or more magnetic disks such as one or more internal hard disks, one or more removable disks, one or more magneto-optical disks, one or more CD-ROM or DVD-ROM disks, etc., on which instructions and/or data may be stored to facilitate the operation of processor 602. Input device 610 may include a keyboard, a mouse, a voice-controlled input device, a touch sensitive input device (e.g., a touch screen), and/or the like for receiving user inputs to apparatus 600.

It should be noted that apparatus 600 may operate as a standalone device or may be connected (e.g., networked or clustered) with other computation devices to perform the tasks described herein. And even though only one instance of each component is shown in FIG. 6, a skilled person in the art will understand that apparatus 600 may include multiple instances of one or more of the components shown in the figure.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. An apparatus, comprising:
one or more processors configured to:
obtain a first set of images of a medical environment and a second set of images of the medical environment, wherein the first set of images is associated with a first viewpoint and the second set of images is associated with a second viewpoint;
determining first semantic information associated with the medical environment based on the first set of images or the second set of images;
generate a multi-dimensional representation of the medical environment based on at least the first set of images, the second set of images, and the first semantic information, wherein the multi-dimensional representation includes multiple views of the medical environment over a time period, a first subset of the multiple views is associated with the first viewpoint, a second subset of the multiple views is associated with the second viewpoint, and at least one of the multiple views of the medical environment includes a presentation of the first semantic information; and
provide the multi-dimensional representation of the medical environment to a receiving device.

2. The apparatus of claim 1, wherein the one or more processors are configured to determine the first semantic information based on a machine-learning model trained for determining a location or a motion of an object or a person in the medical environment based on the first set of images or the second set of images, and wherein the first semantic information indicates the location or motion of the object or person in the medical environment.

3. The apparatus of claim 2, wherein the one or more processors are further configured to determine a phase of a medical procedure being performed in the medical environment based on the location or motion of the object or person in the medical environment, and wherein the first semantic information further indicates the phase of the medical procedure.

4. The apparatus of claim 1, wherein, prior to generating the multi-dimensional representation of the medical environment based on at least the first set of images, the second set of images, and the first semantic information, the one or more processors are further configured to edit one or more identifying features of a person detected in the first set of images or the second set of images to hide an identity of the person.

5. The apparatus of claim 1, wherein, prior to providing the multi-dimensional representation of the medical environment to the receiving device, the one or more processors are further configured to generate a synthetic view of the medical environment based on a machine-learning model and add the synthetic view of the medical environment to the multi-dimensional representation, the synthetic view depicting a scene in the medical environment not shown in the first set of images or the second set of images.

6. The apparatus of claim 5, wherein the first set of images of the medical environment spans a first time period, the second set of images of the medical environment spans a second time period, and the synthetic view of the medical environment is associated with a time spot outside the first time period and the second time period.

7. The apparatus of claim 1, wherein, prior to providing the multi-dimensional representation of the medical environment to the receiving device, the one or more processors are further configured to increase a resolution of at least one of the multiple views of the medical environment based on a machine-learning model.

8. The apparatus of claim 1, wherein, prior to providing the multi-dimensional representation of the medical environment to the receiving device, the one or more processors are further configured to fill a region in at least one of the multiple views of the medical environment based on a machine-learning model.

9. The apparatus of claim 1, wherein, prior to providing the multi-dimensional representation of the medical environment to the receiving device, the one or more processors are further configured to determine second semantic information associated with the medical environment and add the second semantic information to the multi-dimensional representation.

10. The apparatus of claim 9, wherein the second semantic information includes a medical record of a patient, and wherein the one or more processors being configured to determine the second semantic information comprises the one or more processors being configured to determine, based on a machine-learning model, an identity of the patient based on the first set of images or the second set of images, and retrieve the medical record based on the identity of the patient.

11. The apparatus of claim 1, wherein the multi-dimensional representation of the medical environment includes a stereoscopic rendition of the medical environment.

12. A method for recording a medical environment, wherein the method is implemented by a computing apparatus and comprises:
    obtaining a first set of images of the medical environment and a second set of images of the medical environment, wherein the first set of images is associated with a first viewpoint and the second set of images is associated with a second viewpoint;
    determining first semantic information associated with the medical environment based on the first set of images or the second set of images;
    generating a multi-dimensional representation of the medical environment based on at least the first set of images, the second set of images, and the first semantic information, wherein the multi-dimensional representation includes multiple views of the medical environment over a time period, a first subset of the multiple views is associated with the first viewpoint, a second subset of the multiple views is associated with the second viewpoint, and at least one of the multiple views of the medical environment includes a presentation of the first semantic information; and
    providing the multi-dimensional representation of the medical environment to a receiving device.

13. The method of claim 12, wherein the first semantic information is determined based on a machine-learning model trained for determining a location or a motion of an object or a person in the medical environment based on the first set of images or the second set of images, and wherein the first semantic information indicates the location or motion of the object or person in the medical environment.

14. The method of claim 13, further comprising determining a phase of a medical procedure being performed in the medical environment based on the location or motion of the object or person in the medical environment, wherein the first semantic information further indicates the phase of the medical procedure.

15. The method of claim 12, further comprising, prior to generating the multi-dimensional representation of the medical environment based on at least the first set of images, the second set of images, and the first semantic information, editing one or more identifying features of a person detected in the first set of images or the second set of images to hide an identity of the person.

16. The method of claim 12, further comprising, prior to providing the multi-dimensional representation of the medical environment to the receiving device, generating a synthetic view of the medical environment based on a machine-learning model and adding the synthetic view of the medical environment to the multi-dimensional representation, wherein the synthetic view depicts a scene in the medical environment not shown in the first set of images or the second set of images.

17. The method of claim 16, wherein the first set of images of the medical environment spans a first time period, the second set of images of the medical environment spans a second time period, and the synthetic view of the medical environment is associated with a time spot outside the first time period and the second time period.

18. The method of claim 12, further comprising, prior to providing the multi-dimensional representation of the medical environment to the receiving device, increasing a resolution of at least one of the multiple views of the medical environment based on a first machine-learning model or filling a region in at least one of the multiple views of the medical environment based on a second machine-learning model.

19. The method of claim 12, further comprising, prior to providing the multi-dimensional representation of the medical environment to the receiving device, determining second semantic information associated with the medical environment and adding the second semantic information to the multi-dimensional representation, wherein the second semantic information includes a medical record of a patient.

20. The method of claim 12, wherein the multi-dimensional representation of the medical environment includes a stereoscopic rendition of the medical environment.

* * * * *